United States Patent
Doerr (10) Patent No.: US 8,321,001 B2
(45) Date of Patent: Nov. 27, 2012

(54) IMPLANTABLE P-WAVE DISPERSION DETECTOR

(75) Inventor: Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 276 days.

(21) Appl. No.: 12/762,116

(22) Filed: Apr. 16, 2010

(65) Prior Publication Data
US 2010/0286540 A1 Nov. 11, 2010

(30) Foreign Application Priority Data
May 11, 2009 (DE) .......................... 10 2009 002 988

(51) Int. Cl.
*A61B 5/02* (2006.01)
*A61B 5/04* (2006.01)

(52) U.S. Cl. ........ 600/509; 600/508; 600/516; 600/517; 600/518; 600/519

(58) Field of Classification Search .................. 600/508, 600/509, 516–519; 607/9, 14
See application file for complete search history.

(56) References Cited

U.S. PATENT DOCUMENTS

| | | | |
|---|---|---|---|
| 6,292,694 B1 | 9/2001 | Schloss et al. | |
| 6,449,503 B1 | 9/2002 | Hsu | |
| 7,010,346 B1* | 3/2006 | Schloss et al. | 607/14 |
| 2002/0123769 A1* | 9/2002 | Panken et al. | 607/9 |
| 2005/0027321 A1 | 2/2005 | Ferek-Petric | |
| 2006/0173369 A1 | 8/2006 | Kaski | |
| 2008/0114258 A1 | 5/2008 | Zhang et al. | |

OTHER PUBLICATIONS

European Search Report, dated Jul. 30, 2010, 6 pages.
German Search Report for priority application, dated Dec. 9, 2009, 4 pages.
Koide et al. "Usefulness of P-wave dispersion in standard twelve-lead . . . " Am J Cardiol.Sep. 1, 2008;102(5):573-7. Epub Jul. 10, 2008.

* cited by examiner

*Primary Examiner* — Niketa Patel
*Assistant Examiner* — Lindsey G Hankins
(74) *Attorney, Agent, or Firm* — ARC IP Law, PC; Joseph J. Mayo (57) ABSTRACT

An electromedical implant, having
a far-field electrocardiogram capturing unit for recording a far-field electrocardiogram signal, which is connected or can be connected to at least two electrodes for recording electric signals reflecting the curve of the far-field electrocardiogram of the right and left atria,
a detection unit, which is designed to detect signal features characterizing atrial cardiac actions in an electrocardiogram signal,
an averaging unit, which is connected to the recording unit and the detection unit and designed to generate an averaged P-wave signal in that the averaging unit averages a plurality of signal sections of the electrocardiogram signal associated with a particular detected atrial cardiac action, and
an evaluation unit, which is connected to the averaging unit and designed to determine the duration of an averaged P-wave in the particular averaged P-wave signal.

13 Claims, 6 Drawing Sheets

IMPLANTABLE P-WAVE DISPERSION DETECTOR

This application takes priority from German Patent Application DE 10 2009 002 988.5, filed 11 May 2009, the specification of which is hereby incorporated herein by reference.

BACKGROUND OF THE INVENTION

1. Field of the Invention

One or more embodiments of the invention relates to an electromedical implant designed for determining P-wave dispersion. The electromedical implant can, for example, be an appropriately configured implantable pacemaker or an implantable cardioverter/defibrillator (ICD), or a combination of both.

2. Description of the Related Art

Electromedical implants include a recording unit for recording an electrocardiogram signal. This recording unit is connected, or can be connected, to at least two electrodes for recording electric signals, which reflect the curve of an electrocardiogram signal of the right and left atria.

In addition, the electromedical implant comprises a detection unit, which is designed to detect signal features characterizing atrial cardiac actions in an electrocardiogram signal. The latter is performed in known implantable pacemakers or ICD in that an intra-atrial electrocardiogram signal recorded in the atrium of a heart is permanently subjected to a threshold value comparison. If the amplitude of the intra-atrial electrocardiogram signal exceeds the threshold value, an atrial cardiac action is detected. Typically, an atrial sensing unit is provided for this purpose. The detection of an atrial cardiac action is also referred to an atrial sense event. The respectively detected electric signal is the result of a depolarization of the atrial muscle cells accompanying the contraction of the atrial myocardium.

Detecting and evaluating the atrial dispersion are likewise known in principle. The P-wave dispersion describes the temporal distribution of the P-wave in the 12 leads of the surface electrocardiogram and is therefore an expression of atrial excitation propagation. If the P-wave dispersion value increases, it can be assumed that inhomogeneous atrial excitation formation and conduction are present. In particular atrial excitation initiated by several focuses prior to atrial arrhythmia causes inhomogeneous excitation of the atrium and consequently greater P-wave dispersion.

P-wave dispersion therefore provides important diagnostic information for patients at risk of atrial arrhythmia. Since the coincidence of atrial fibrillation and the indication for an ICD are very high, this parameter is of tremendous importance for these patients.

US 2005/0027321 A1 describes an apparatus which, among other things, can determine the morphology of the P-wave, including the duration thereof, and is also intended to record the dispersions of widths of the P-waves. The dispersion term is used slightly differently in US 2005/0027321 A1: here, the comparison of the variance of the P-wave width recorded over several consecutive P-waves is meant.

P-wave dispersion described in the literature, however, in the 12-channel surface electrocardiogram is defined as a temporal "scattering" of a P-wave measured in the 12 leads of the surface electrocardiogram. This P-wave dispersion is therefore an expression of the atrial excitation formation and propagation. This is for example what is to be implemented with one or more embodiments of the invention in an electronic implant, without making an atrial electrode absolutely necessary as will be explained in the remainder of this disclosure.

The study "Koide Y, Yotsukura M, Ando H, Aoki S, Suzuki T, Sakata K, Ootomo E, Yoshino H. "Usefulness of P-wave dispersion in standard twelve-lead electrocardiography to predict transition from paroxysmal to persistent atrial fibrillation." Am J. Cardiol. 2008 Sep. 1; 102(5):573-7. Epub 2008 Jul 10" reports of the diagnostic values of P-wave dispersion derived from the 12-channel surface electrocardiogram.

So far, it has not been possible to automatically capture this parameter in an ICD.

BRIEF SUMMARY OF THE INVENTION

It is the object of one or more embodiments of the invention to capture a parameter in an implantable device (such as ICD, pacemaker, heart rhythm monitor) that corresponds to the P-wave dispersion of the 12-channel surface electrocardiogram, thereby providing a predictive diagnostic value for managing patients with atrial fibrillation.

The key in doing so in one or more embodiments is the exact determination of the earliest onset of atrial excitation and the end of atrial excitation.

According to one or more embodiments of the invention, this object is achieved by an electromedical implant which comprises a far-field electrocardiogram capturing unit for recording a far-field electrocardiogram signal, wherein the unit is connected, or can be connected, to at least two electrodes for recording such electric signals which reflect the curve of a far-field electrocardiogram of the right and left atria. In addition, the electromedical implant according to one or more embodiments of the invention comprises a detection unit, which is designed to detect signal features characterizing atrial cardiac actions in an electrocardiogram signal. The electromedical implant further comprises an averaging unit, which is connected to the recording unit and the detection unit and designed to generate an averaged P-wave signal in that the averaging unit averages a plurality of signal sections of the far-field electrocardiogram signal associated with a particular detected atrial cardiac action. Finally, the electromedical implant comprises an evaluation unit, which is connected to the averaging unit and designed to determine the duration of an averaged P-wave in the particular averaged P-wave signal.

The duration of a particular averaged P-wave reflects the dispersion of the P-wave.

One or more embodiments of the invention is based on the realization that a far-field electrocardiogram signal, which is recorded by way of an implant and reflects the activities of both atria, is especially suited for analysis with respect to P-wave dispersion.

In the implants known from the prior art, the analysis of P-waves is typically based on an intra-atrial electrocardiogram, which is recorded using an electrode having a relatively small surface in an atrium of a heart. Such electrocardiograms usually substantially reflect the activity of a single atrium, but not of both atria.

The advantage of the solution according to one or more embodiments of the invention is that now the diagnostic information of P-wave dispersion can be captured in an electronic implant, such as a pacemaker, an ICD, or an implantable monitor. For this purpose, electrodes already present for the typical applications of such a device can be employed.

Using this diagnostic information, patients with atrial fibrillation can be managed considerably better because now continuous monitoring the P-wave dispersion is possible and, for example, the time of a switch in medication or atrial fibrillation ablation can be anticipated and planned.

This additional atrial diagnostics can also contribute to a more customized use of atrial fibrillation ablation and consequently lower the costs for the ablation procedure, which presently are still too high.

Below, a few advantageous embodiments will be explained in detail.

The detection unit for capturing atrial cardiac actions can be a conventional atrial sensing unit, which can be connected to a conventional atrial electrode. The detection unit, however, is preferably connected to the far-field electrocardiogram capturing unit and designed to detect atrial cardiac actions, for example on the basis of morphology criteria, or other criteria, in the far-field electrocardiogram recorded by the far-field electrocardiogram capturing unit. The latter variant has the advantage that it enables the P-wave dispersion to be captured and analyzed even for such implants which have no dedicated atrial electrode, these being single-chamber pacemakers or single-chamber ICDs, for example.

The electrocardiogram supplied to the detection unit is preferably filtered. For this purpose, the implant preferably has a band pass filter, which is matched to the frequency range of the signals to be detected.

In order to record a far-field electrocardiogram signal, the far-field electrocardiogram capturing unit is preferably connected at least to an electrically conductive part of a housing of the implant by way of a first electrode. For one, this allows a far-field electrocardiogram to be recorded, because the housing of the implant is located outside of the heart at a suitable distance. In addition, this variant eliminates the need to implant a separate electrode.

Furthermore, it is preferred to connect the far-field electrocardiogram capturing unit to a defibrillation electrode on an appropriate electrode lead connected to the implant as the second electrode. Defibrillation electrodes are generally designed as shock coils and have a relatively large surface, compared to typical stimulation or sensing electrodes. An atrial shock coil is an electrode that is particularly well suited. By providing an electrode having a large surface as the second electrode for recording a far-field electrocardiogram, the electrocardiogram that is recorded is in fact a far-field electrocardiogram.

The implant is preferably an ICD, connected to the usual electrodes.

Specifically in this case (but also for other implants), the far-field electrocardiogram capturing unit can also be connected to atrial or ventricular ring or tip electrodes, which are known per se, for example the following configurations are possible:

The broad band derivation of the far-field electrocardiogram for determining the P-wave signal is carried out between a distal shock electrode and the housing of an ICD.

The broad band derivation of the far-field electrocardiogram for determining the P-wave signal is carried out between a proximal shock electrode and the housing of an ICD.

The broad band derivation of the far-field electrocardiogram for determining the P-wave signal is carried out between a right ventricular ring electrode and the housing of an ICD or pacemaker.

The broad band derivation of the far-field electrocardiogram for determining the P-wave signal is carried out between a right ventricular tip electrode and the housing of an ICD or pacemaker.

It is also advantageous when the electrode configurations used for the broad band derivation of the far-field electrocardiogram for determining the P-wave dispersion can be manually switched or reprogrammed.

Alternatively, it may be provided that that the respective electrode configuration used for the broad band derivation of the far-field electrocardiogram for determining the P-wave dispersion is automatically selected on the basis of an electrocardiogram signal quality analysis.

The evaluation unit preferably comprises both a unit for determining a starting time of an averaged P-wave and a unit for determining an ending time of an averaged P-wave. These two units can also be provided separately from the evaluation unit and connected thereto. The evaluation unit is designed to determine the duration of an averaged P-wave as a time difference between the starting time determined by the one unit and the ending time determined by the other unit. These two units for determining the starting time and the ending time of an averaged P-wave are preferably designed such that in each case for individual detection parameters, such as signal amplification factor, threshold values, signals used, and the like, can be specified for them. The specification to be selected may also include evaluation of a defined electrocardiogram signal among several regarding the respective time.

It is particularly advantageous when the averaging unit, the evaluation unit, or the unit for determining an ending time of an averaged P-wave is designed to subtract an isochronous ventricular electrocardiogram from a particular P-wave, or a signal section to be averaged, which is to say to subtract the amplitude of a synchronous ventricular electrocardiogram from the respectively corresponding amplitude of the P-wave or the signal section to be averaged.

The averaging unit is preferably designed to average signal sections to be averaged with one another such that they are synchronized with one another over the respective points of time of the detection of an atrial cardiac action. The time of detection of a particular atrial cardiac action is therefore the reference time for averaging the signal sections with one another for all signal sections to be averaged.

With respect to the averaging unit, the number of consecutive signal sections to be averaged can preferably be set.

According to a preferred variant, the implant comprises a monitoring unit, which monitors a parameter that corresponds to the P-wave dispersion—which is to say, in particular the duration of the averaged P-waves determined by the evaluation unit—at regular intervals, preferably continuously or at least once a day.

It is particularly advantageous to design the far-field electrocardiogram capturing unit such that at least two far-field electrocardiogram signals can be recorded simultaneously, as is explained below with respect to at least the final two figures of the specification described in the next section.

According to a further advantageous variant, a broad band derivation of the far-field electrocardiogram for determining the P-wave dispersion is carried out by way of a right atrial, floating electrode (VDD principle).

BRIEF DESCRIPTION OF THE DRAWINGS

One or more embodiments of the invention will now be described in more detail with reference to an exemplary embodiment illustrated the figures. The figures show.

DETAILED DESCRIPTION OF THE INVENTION

Figure 1:
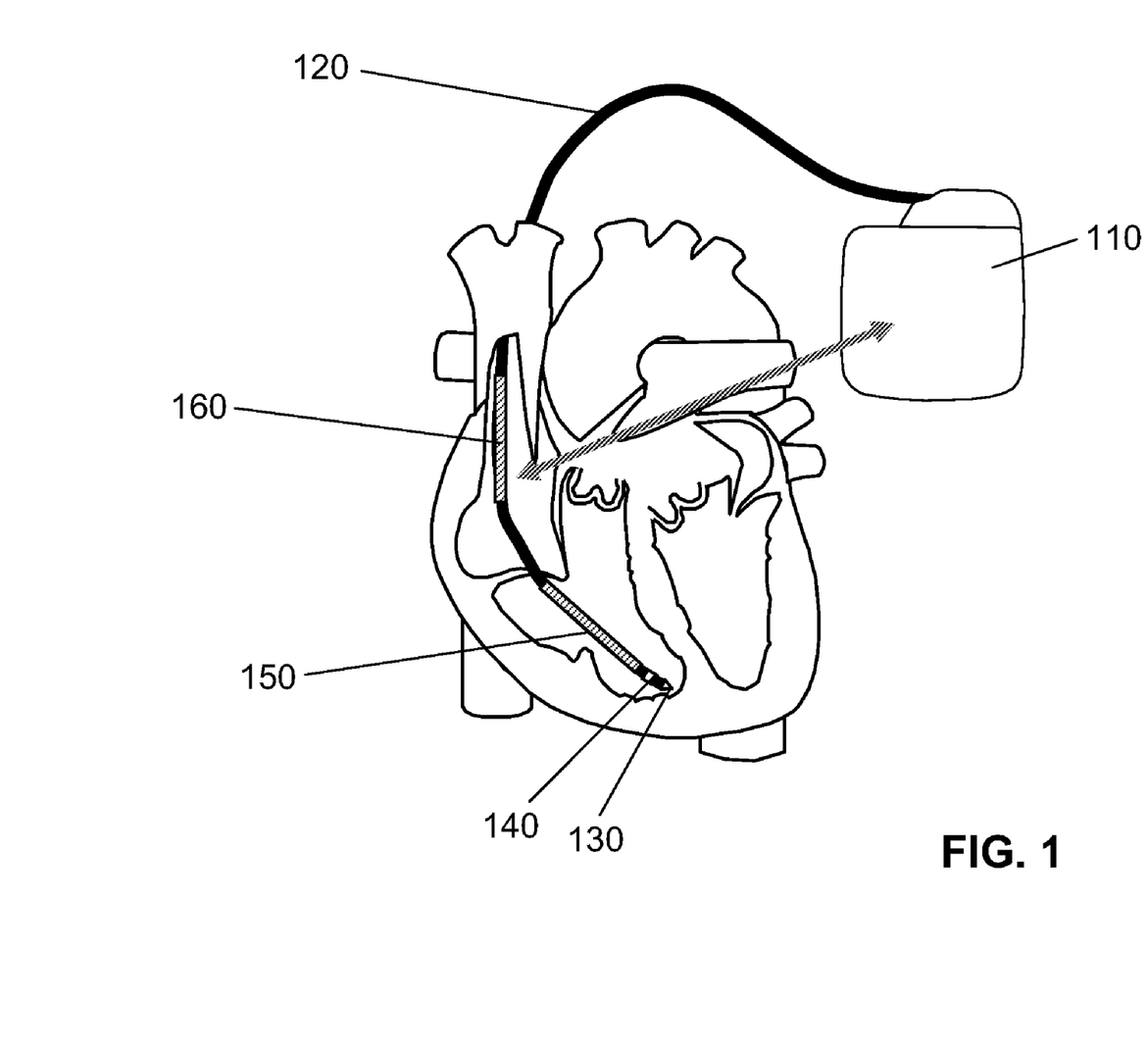
FIG. 1: a single-chamber ICD system as an example of an electromedical implant.

As a possible embodiment, FIG. 1 shows a single-chamber ICD system. The housing 110 thereof, including the components provided therein, is connected to a flexible, implantable electrode lead 120. At the distal end thereof, the lead has a bipolar perception and stimulation pole, comprising a right ventricular tip electrode 130 and a right ventricular ring electrode 140. For delivering the defibrillation shock, a distal shock coil 150, and optionally a proximal shock coil 160, are provided at the electrode lead 120 as the respective defibrillation or shock electrode.

The electrocardiograms required for the determination of the P-wave dispersion as claimed can in principle be derived from the following electrode combinations:

Variant A: right ventricular tip electrode —ICD housing
Variant B: right ventricular ring electrode —ICD housing
Variant C: distal shock coil —ICD housing
Variant D: proximal shock coil —ICD housing The preferred derivations, however, are variant D, if a proximal shock coil is present, and variant C, if no proximal shock coil is present, since in these derivations the imaging of the atrial excitation (P-wave) is the most favorable.

Since several derivations are possible for determining the P-wave, in the exemplary embodiment a selection matrix is provided, which selects the most favorable derivation of the P-wave determination, either manually and programmably by the user, or automatically on the basis of electrode impedances and signal quality.

In the version as a pacemaker, the illustrated shock coils 150 and 160 are eliminated. Instead, the electrocardiogram derivation is performed by way of an atrial pacemaker electrode (optionally tip electrode or ring electrode), or by way of a floating atrial electrode, which additionally is accommodated as a ring electrode on the feed line of the ventricular electrode (A+ or VDD principle).

Figure 2:
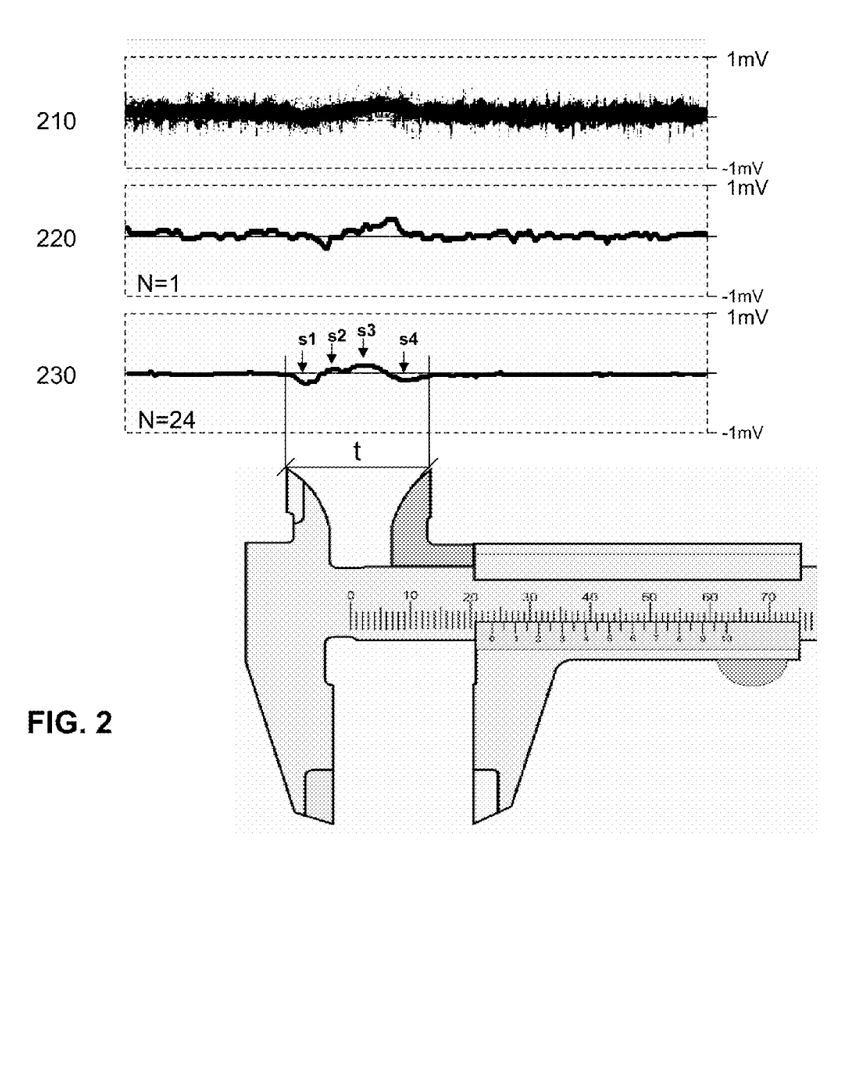
FIG. 2: an exemplary illustration of a P-wave in a far-field electrocardiogram.

FIG. 2 shows the results of signal averaging for detection of a P-wave in the far-field electrocardiogram.

The upper curve 210 shows an input signal having an amplitude of 0.1 mV in order to simulate a very small P-wave. In addition, the input signal is slightly noisy in order to simulate the actual conditions of the far-field electrocardiogram derivation.

In the second curve 220, the derivation of these P-waves in the far-field electrocardiogram is shown, derived with an ICD between the proximal shock coil and the housing of the ICD. The interference signals illustrated next to the P-wave do not allow any automatic P-wave detection by the ICD.

In the third curve 230, the signal is shown after it has been averaged over 24 cardiac cycles. Signal averaging is synchronized for a particular detected atrial cardiac action (atrial sense event). The atrial cardiac action in this embodiment is detected in an electrocardiogram which was recorded by the proximal shock electrode 160 and the housing of the implant 110. Alternatively, a separate right atrial electrode can be used for atrial sensing.

After 24 averagings (signal 230), the signal quality is already sufficient to be able to achieve automatic detection the P-wave, including the components thereof (right-left atria), in the ICD.

Based on the sufficiently averaged signal 230, it is now possible to determine parameters which correlate with the P-wave dispersion. The most important parameter is the duration (t) (also referred to as width) of the P-wave, which is determined in the implant and stored. If the derivation vector and number of averaged cycles are sufficient, the duration of the averaged P-wave corresponds to the P-wave dispersion from the 12-channel surface electrocardiogram.

Further improvement in the diagnostic meaningfulness—particularly for unmasking several focuses of the atrial excitation—is achieved by counting the points of irregularities (S1 . . . S4) in the averaged P-wave 230.

Figure 3:
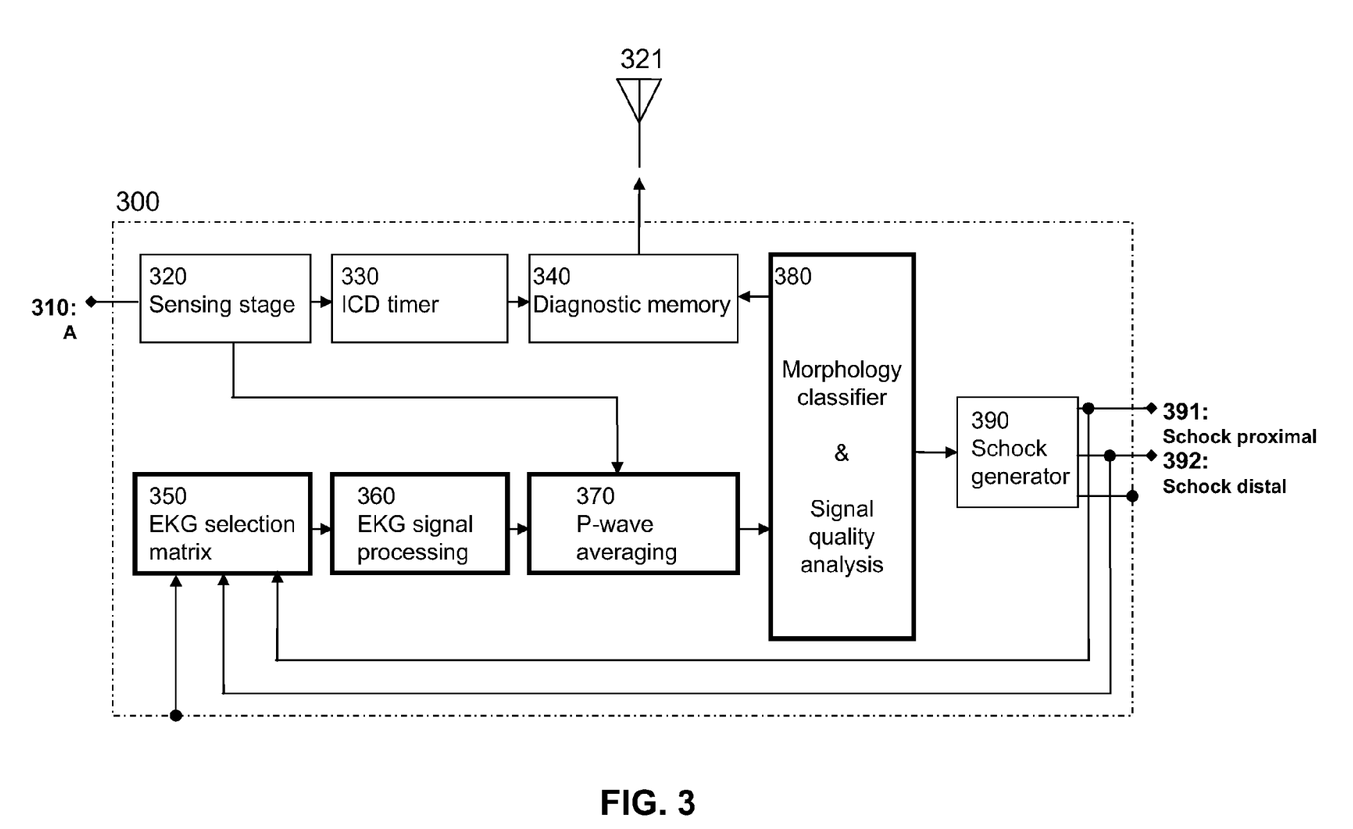
FIG. 3: a block diagram of several components of an implant.

FIG. 3 shows several components of an ICD, which is designed for a P-wave dispersion analysis described according to one or more embodiments of the invention, shown in the form of a block diagram.

The ICD here is additionally connected to a right atrial perception and stimulation electrode 310. The intracardiac electrocardiogram (IEGM) recorded (derived) with the help of this electrode is analyzed in a conventional ICD sensing stage 320, and the detected atrial cardiac actions (atrial events, P-sense) are subsequently supplied to an ICD timer 330 for therapy control and rhythm diagnostic 340.

Not shown is the ventricular perception and stimulation channel, because it is not changed compared to the prior art for the implementation according to embodiments of the invention.

The shock electrodes 391 and 392 connected to a shock generator 390 of the ICD, and the electrically conductive housing 300 of the ICD, are additionally connected to a far-field electrocardiogram selection matrix 350. This selection matrix 350 establishes which of the electrodes are used for the derivation (recording) of a far-field electrocardiogram for the P-wave dispersion analysis. The selection is made either manually by programming by the physician, or automatically by a signal quality analysis conducted in the ICD (380: "signal quality analysis"). This far-field electrocardiogram is subsequently preprocessed (amplified, digitized, filtered) in an electrocardiogram signal processing unit 360 and then fed to an average value forming device 370 as the averaging unit. The far-field electrocardiogram selection matrix 350 and the electrocardiogram signal processing unit 360 together form a far-field electrocardiogram capturing unit. The average value forming device 370 connected thereto conducts triggered signal averaging for a particular detected atrial cardiac action (atrial event 320), and supplies these averaged P-wave recordings to a morphology classifier 380. This morphology classifier 380 measures these averaged P-wave with respect to the signal duration (signal width) thereof, optionally with respect to the number of points of irregularities and optionally other morphological characteristics. This information is then supplied to a diagnostic memory 340, wherein an association with the atrial rhythm (330->340) is maintained.

The information on the P-wave dispersion and on the atrial rhythm available in the diagnostic memory 340 can then be transmitted and displayed to the physician by way of near-field or far-field telemetry 321.

Figure 4:
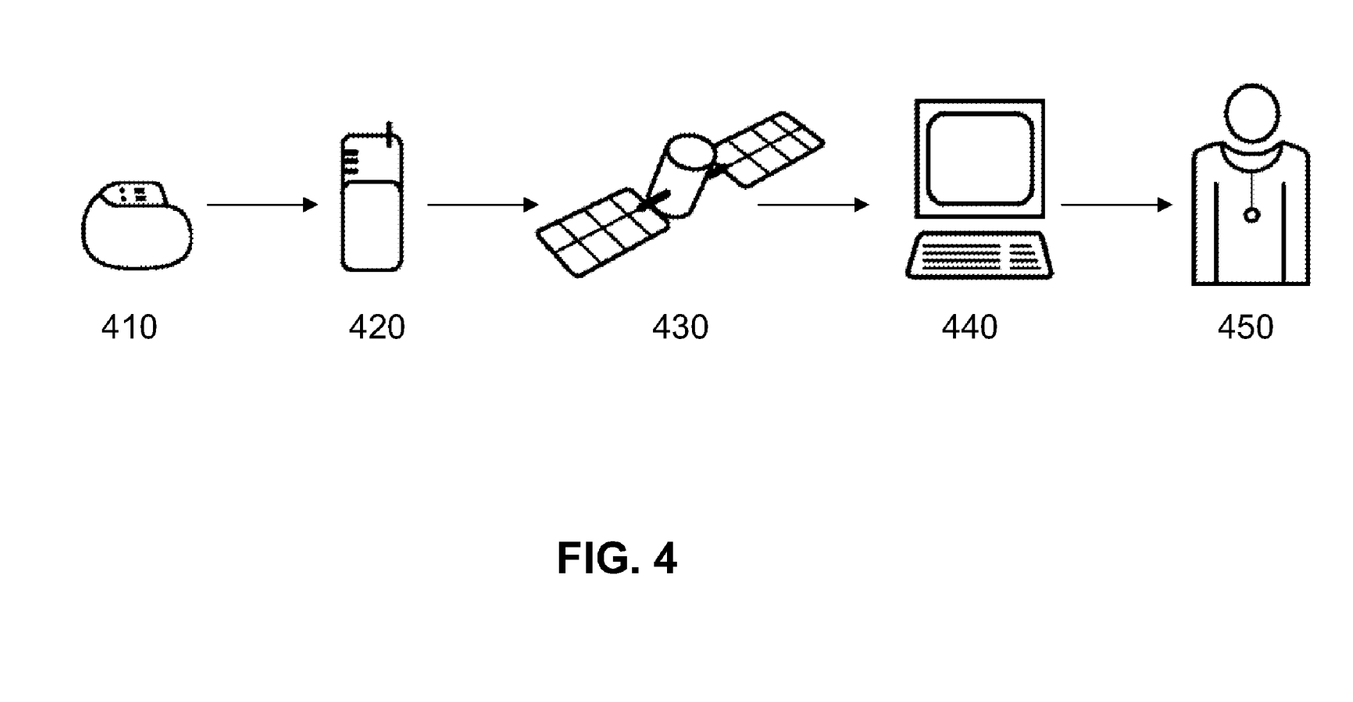
FIG. 4: an example of an implant in a remote transmission system.

FIG. 4 shows an expanded overall system for continuous monitoring of the P-wave dispersion. Here, the electronic implant 410 described above is connected to a relay station or a base station 420 by way of RF telemetry (preferably in the MICS band) and periodically transmits this information relating to the absence of atrial fibrillation to this relay station 420. This station in turn transmits the information via a data transmission network 430 to a remote monitoring server 440 to which the physician 450 has access, for example via Internet, and therefore has the option to care for the patient by telemedicine (such as drug monitoring, scheduling for ablation therapy).

Optionally, following a renewed occurrence of atrial fibrillation, or a period during which the criteria for the verification of the absence of atrial fibrillation are not met, the implant can immediately send a message to the remote monitoring system, and the remote monitoring server then sends a special message to the attending physician (such as in the form of SMS, fax, e-mail, or particularly striking identification of the patient in the remote continuing care database).

In order to ensure correct analysis of the classified rhythm by the physician, during the events classified as periods not free of atrial fibrillation a stored IEGM is also sent to the remote monitoring server.

Figure 5:
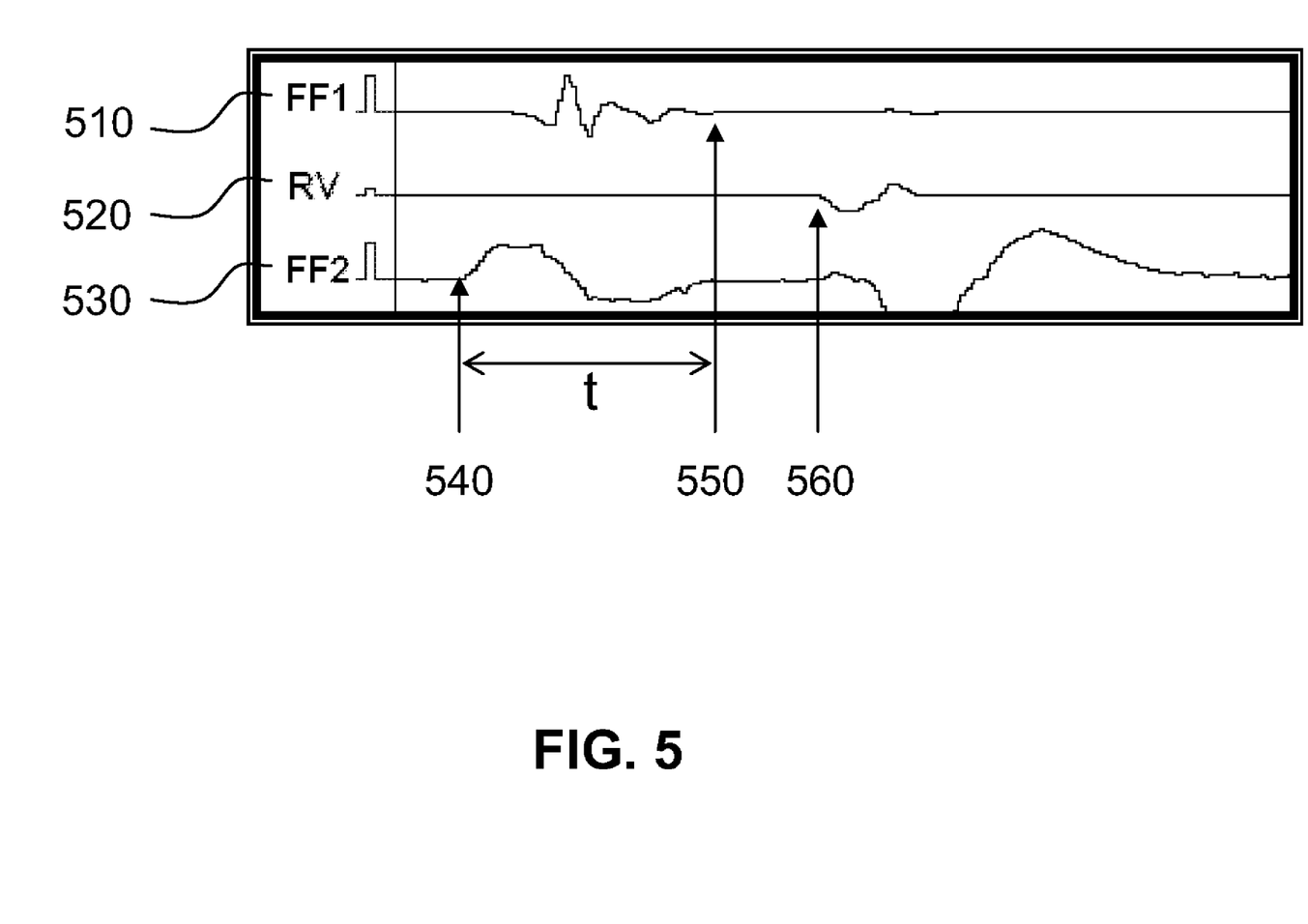
FIG. 5: an example of a multichannel P-wave duration determination.

In FIG. 5, a multichannel determination of the P-wave width ("dispersion") is illustrated by way of example. In this example, a first far-field electrocardiogram derivation 510 is recorded and averaged, and simultaneously a second far-field electrocardiogram derivation 530 is recorded and averaged. Both far-field electrocardiogram derivations are selected such that the atrial electrocardiogram can be depicted well. In addition, the right ventricular (alternatively the left ventricular) derived intracardiac electrocardiogram 520 is also recorded. The P-wave duration is now determined such that the earliest onset 540 of atrial excitation is searched for in both averaged atrial derivations. Subsequently, the end 550 of the atrial excitation in the two averaged atrial electrocardiograms is determined. Since typically also the ventricular excitation is visible in the atrial far-field electrocardiogram, additionally the analysis window for the atrial excitations is limited to the back. For this purpose, the information from the ventricular IEGM is used. The atrial analysis window is limited at the earliest verifiable ventricular excitation 560.

Figure 6:
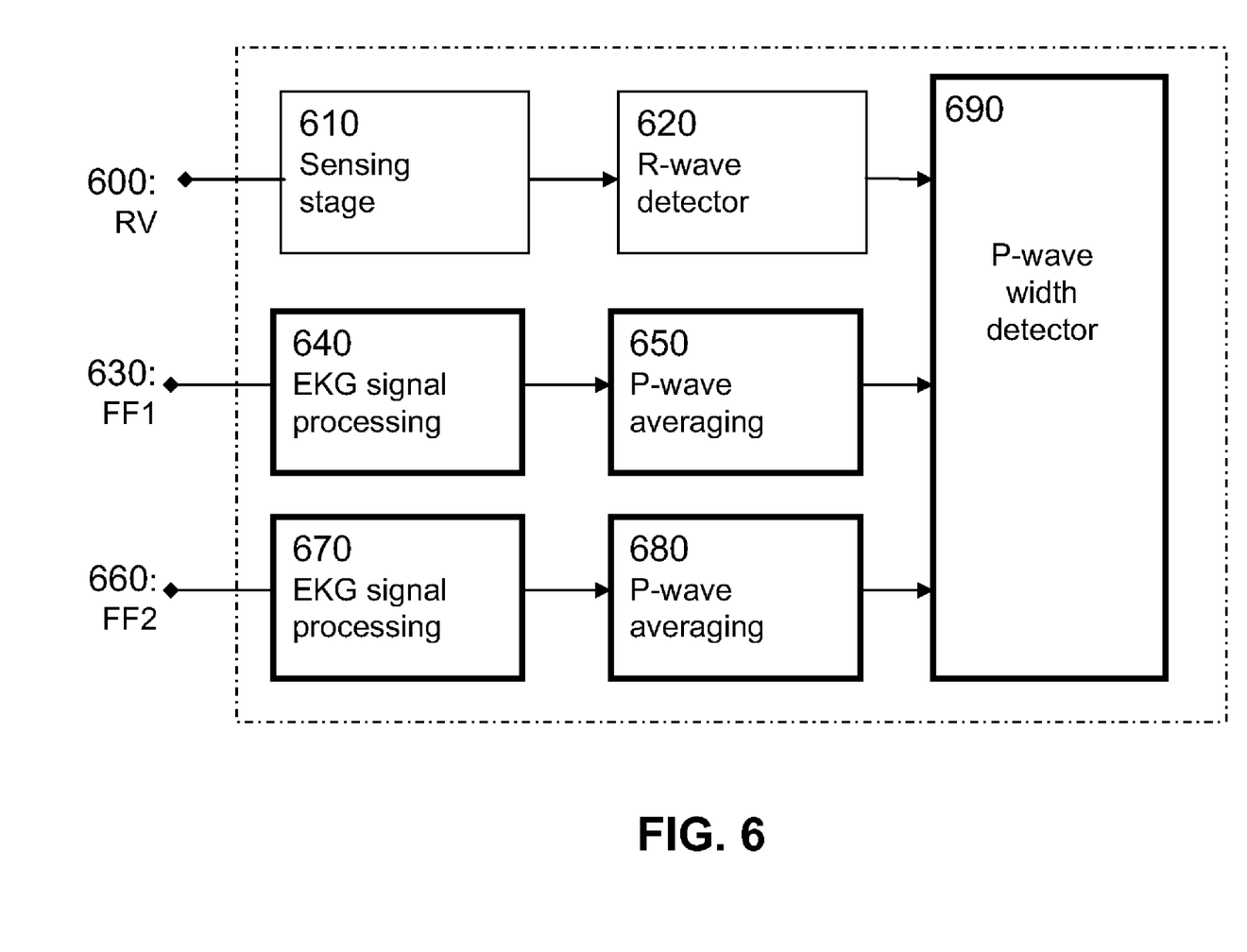
FIG. 6: a multichannel detector for P-wave duration determination.

FIG. 6 shows a multichannel detector for determining the P-wave width according to the method illustrated in FIG. 5. This detector is connected to a right ventricular electrode (600: RV), electrodes for a first far-field derivation (630: FF1), and electrodes for a second far-field derivation (660: FF2). The electrodes for the first far-field derivation can be, for example, the proximal shock coil of an ICD electrode and the ICD housing. The electrodes for the second far-field derivation can be, for example, the proximal ring of a coronary sinus electrode and the ICD housing.

The right ventricular electrode connection is connected to a conventional sensing stage 610 for IEGM signal processing. This unit in turn forwards the processed IEGM signals to an R-wave detector, which is designed such that it detects the earliest onset of the R-wave and then forwards it to the connected R-wave width detector 690.

The two far-field connections 630 and 660 are connected to an electrocardiogram signal processing unit 640 and 670, respectively. These electrocardiogram signal processing units 640 and 670 are designed such that they maximally amplify the atrial signals to be captured and subject them to broadband filtration, so that the entire atrial excitation can be captured. For the electrocardiogram signal processing of the first far-field channel 640, other parameters can be set than for the electrocardiogram signal processing unit of the second far-field channel 670. Optionally, the electrocardiogram signal processing units may contain algorithms, which conduct automatic beat-to-beat adjustment of the parameters in order to optimally capture the recorded electrocardiogram signals.

The far-field electrocardiogram signal processing units are associated with a P-wave averaging unit 650 and 680. These units average the atrial electrocardiogram over a defined number of cardiac cycles, wherein this number is either fixed and preset or automatically determined by a signal quality analysis (such as based on the evaluation of the signal-to-noise ratio). The results of the P-wave averaging (650, 680) are likewise supplied to the P-wave width detector (690). This P-wave width detector then determines the duration of the P-wave in accordance with the description of FIG. 5.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An electromedical implant, comprising
at least two electrodes configured to
record electric signals that reflect a curve of a far-field electrocardiogram signal of a right and left atria of a heart;
a far-field electrocardiogram capturing unit configured to
record a first far-field electrocardiogram signal and record a second far-field electrocardiogram signal between different electrodes of said at least two electrodes,
wherein said far-field electrocardiogram capturing unit is connected or can be connected to the at least two electrodes;
a detection unit, which is configured to
detect signal features that characterize atrial cardiac actions in an electrocardiogram signal;
an averaging unit, which is connected to the far-field electrocardiogram capturing unit and the detection unit and is configured to
average a plurality of signal sections of the first far-field electrocardiogram signal associated with a particular detected atrial cardiac action to generate a first averaged P-wave signal associated with the first far-field electrocardiogram signal;
average a plurality of signal sections of the second far-field electrocardiogram signal associated with a particular detected atrial cardiac action to generate a second averaged P-wave signal associated with the first far-field electrocardiogram signal;
determine the earliest onset of atrial excitation through a search of said first averaged P-wave signal and said second averaged P-wave signal; and,
an evaluation unit, which is connected to the averaging unit and which is configured to
determine a duration of an averaged P-wave in a particular averaged P-wave signal based on said earliest onset of said atrial excitation in said first averaged P-wave signal and said second averaged P-wave signal.

2. The electromedical implant according to claim 1, wherein the detection unit is connected to the far-field electrocardiogram capturing unit, or is part thereof, and wherein said detection unit is configured to detect the signal features that characterize the atrial cardiac actions in the electrocardiogram signal recorded by the far-field electrocardiogram capturing unit.

3. The electromedical implant according to claim 1, wherein the detection unit is configured to detect the signal features that characterize the atrial cardiac actions in a filtered electrocardiogram signal.

4. The electromedical implant according to claim 1, further comprising a housing having an electrically conductive section, wherein the far-field electrocardiogram capturing unit is connected to the electrically conductive section of the housing of the electromedical implant as a first of the at least two electrodes.

5. The electromedical implant according to claim 4, further comprising a defibrillation electrode configured for intracardiac positioning, wherein the far-field electrocardiogram capturing unit is connected to the defibrillation electrode as the second of the at least two electrodes.

6. The electromedical implant according to claim 1, wherein the evaluation unit comprises a first unit configured to determine a starting time of the averaged P-wave and comprises a second unit configured to determine an ending time of the averaged P-wave wherein said evaluation unit is configured to determine the duration of the averaged P-wave as a time difference between the starting time and ending time.

7. The electromedical implant according to claim 6, wherein separate detector parameters can be specified for said first unit configured to determine the starting time of the averaged P-wave and for said second unit configured to determine the ending time of the averaged P-wave.

8. The electromedical implant according to claim 6, wherein the averaging unit, the evaluation unit, or the second unit configured to determine the ending time of the averaged P-wave is configured to subtract an isochronous ventricular electrocardiogram from a particular P-wave or from a signal section to be averaged.

9. The electromedical implant according to claim 1, wherein the averaging unit is configured to average said plurality of signal sections of said first and said second far-field electrocardiograms with one another respectively such that they are synchronized with one another over respective times of detection of an atrial cardiac action of each signal section.

10. The electromedical implant according to claim 1, wherein the averaging unit is configured to average a settable number of consecutive signal sections with one another.

11. The electromedical implant according to claim 1, further comprising a monitoring unit, which is connected to the evaluation unit and which is configured to monitor a parameter that corresponds to a P-wave dispersion at regular intervals.

12. The electromedical implant according to claim 1, wherein the far-field electrocardiogram capturing unit is configured to record at least two far-field electrocardiogram signals at a same time.

13. The electromedical implant according to claim 1, further comprising a right atrial, floating electrode, wherein the far-field electrocardiogram capturing unit is configured to record a broad band far-field electrocardiogram by way of the right atrial, floating electrode.

* * * * *